(12) United States Patent
Perret et al.

(10) Patent No.: US 10,864,017 B2
(45) Date of Patent: Dec. 15, 2020

(54) ORTHOPAEDIC ATTACHMENT DEVICE

(71) Applicant: GEXFIX SA, Carouge-Geneve (CH)

(72) Inventors: Jean-Pierre Perret, Thyez (FR); Filadelfio Marletta, Grancia (CH)

(73) Assignee: GEXFIX SA

( * ) Notice: Subject to any disclaimer, the term of this patent is extended or adjusted under 35 U.S.C. 154(b) by 0 days.

(21) Appl. No.: 16/069,402

(22) PCT Filed: Jan. 12, 2017

(86) PCT No.: PCT/EP2017/050533
§ 371 (c)(1),
(2) Date: Dec. 26, 2018

(87) PCT Pub. No.: WO2017/121781
PCT Pub. Date: Jul. 20, 2017

(65) Prior Publication Data
US 2019/0110815 A1 Apr. 18, 2019

(30) Foreign Application Priority Data
Jan. 15, 2016 (FR) .................... 16 50307

(51) Int. Cl.
*A61B 17/64* (2006.01)
(52) U.S. Cl.
CPC ...... *A61B 17/6466* (2013.01); *A61B 17/6416* (2013.01)
(58) Field of Classification Search
CPC ..... A61B 17/60; A61B 17/64; A61B 17/6416; A61B 17/6466
See application file for complete search history.

(56) References Cited

U.S. PATENT DOCUMENTS

| 8,277,448 B2 | 10/2012 | Daluiski et al. |
| 8,523,858 B2 | 9/2013 | Lessig et al. |

(Continued)

FOREIGN PATENT DOCUMENTS

| DE | 299 22 734 | 5/2000 |
| EP | 0 806 185 A1 | 11/1997 |

(Continued)

OTHER PUBLICATIONS

International Search Report (with English translation) dated Apr. 12, 2017 for International Application No. PCT/EP2017/050533.

(Continued)

*Primary Examiner* — Julianna N Harvey
(74) *Attorney, Agent, or Firm* — Fay Sharpe LLP

(57) ABSTRACT

An orthopaedic attachment device (1) which can adopt at least two positions, an inoperative position and a locked position. The orthopaedic attachment device comprises two clamps (2a, 2b) mounted opposite each other through a resilient member, and held by a clamping rod along a median axis by through-holes. Each of the clamps (2a, 2b) comprises a body part that comprises a outer jaw (4b) and an inner jaw (4a), connected by a joining wall (5), and which defines an opening that is designed to accommodate a stiffening bar or a pin via an insert. The opening extends inwards from the clamp (2a, 2b) as far as the joining wall (5) towards a passage and a hinge region. In the inoperative position, the outer jaw (4b) is fixed, whereas the inner jaw (4a) is moveable inwards towards the resilient member.

19 Claims, 4 Drawing Sheets

(56) References Cited

U.S. PATENT DOCUMENTS

| | | |
|---|---|---|
| 9,138,260 B2 | 9/2015 | Miller et al. |
| 2002/0042613 A1 | 4/2002 | Mata |
| 2006/0039750 A1* | 2/2006 | Thomke ............... A61B 17/645 |
| | | 403/385 |
| 2007/0038217 A1 | 2/2007 | Brown et al. |

FOREIGN PATENT DOCUMENTS

| | | |
|---|---|---|
| EP | 1 627 608 A1 | 2/2006 |
| EP | 1 935 357 A1 | 6/2008 |
| EP | 2 319 436 A1 | 5/2011 |
| EP | 2 465 454 A1 | 6/2012 |

OTHER PUBLICATIONS

Written Opinion dated Apr. 12, 2017 for International Application No. PCT/EP2017/050533.
International Preliminary Report on Patentability (with English translation) dated Mar. 12, 2018 for International Application No. PCT/EP2017/050533.

* cited by examiner

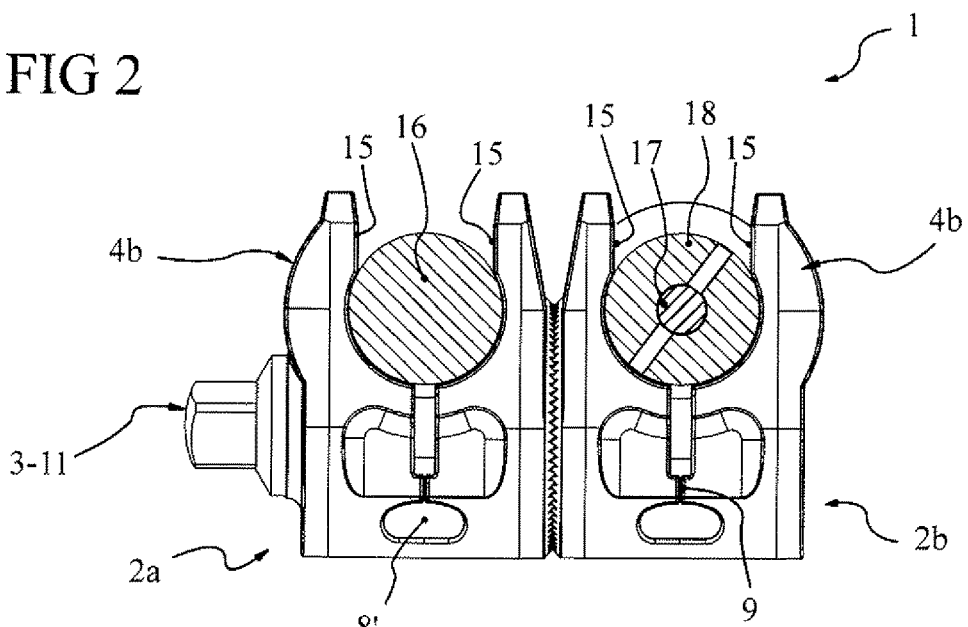
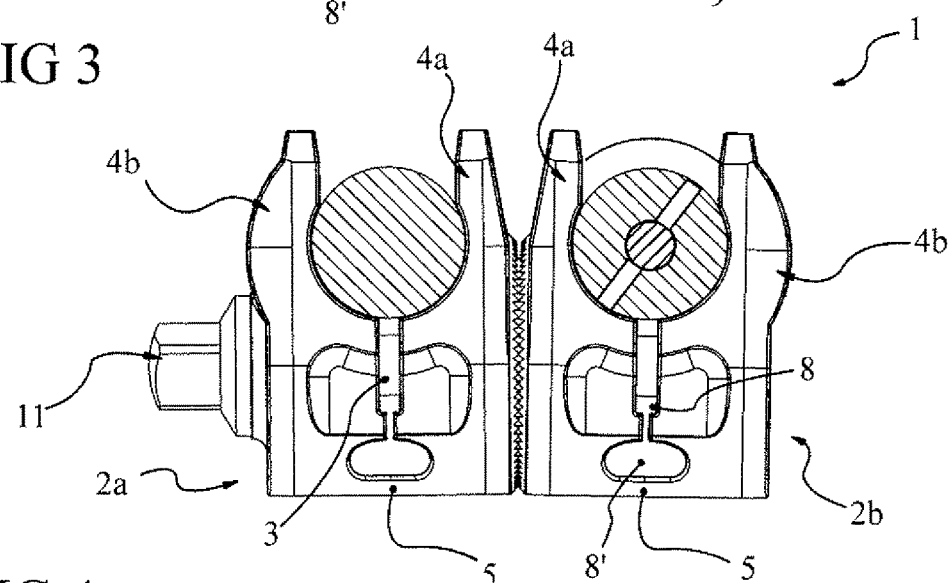
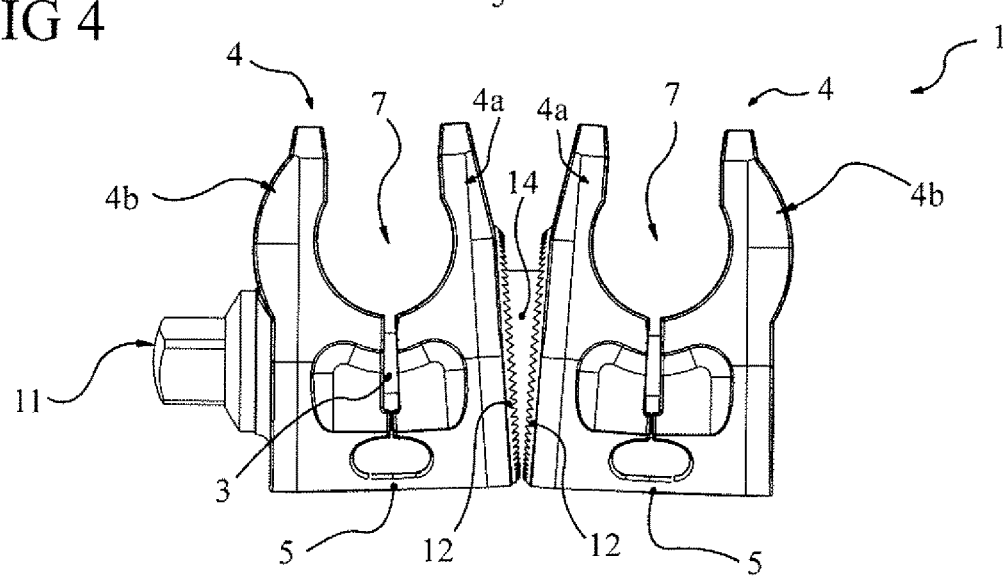

ORTHOPAEDIC ATTACHMENT DEVICE

FIELD OF INVENTION

The present invention concerns an orthopaedic attachment device for external fixators.

BACKGROUND

An external orthopaedic fixator for shortening and lengthening bone fragments is generally comprised of fastening clamps in combination with a stiffening bar that connect the pins affixed inside the parts of bones being treated.

Surgical methods for the installation of an external fixator generally consist of inserting pins into the bones to be shortened or lengthened, of the application of joints and stiffening bars, the adjustment of length and angle, and finally, the locking of the various mechanical components.

Usually an attachment and jointure device is articulated around two fastening clamps formed by an assembly of independent jaws connected by a threaded rod, as disclosed by documents EP 0 806 185, EP 1 935 357, EP 2 465 454, U.S. Pat Nos. 8,277,448, 8,523,858 and 9,138,260. The jaws of a clamp are locked in rotation, such as by a tenon engaged in a mortise, whereas maintaining the position and attaching rods and pins is achieved by locking the rod that goes through the fastening clamps.

To simplify these orthopaedic attachment devices, single-block clamps have been developed, such as those disclosed by documents EP 2 319 436, EP 1 627 608 and US 2007/0038217. These clamps are formed by two jaws arranged opposite each other, connected by a wall, forming a hinge. A clamping rod connects two clamps arranged opposite each other.

The jaws of these clamps are arranged perpendicularly to the clamping rod that goes through them. The major drawback of these clamps is that a pin or a bar may be inserted laterally, by sliding, after attaching the clamps to the rod, or frontally, by clipping on, before assembling the clamps to the clamping rod. Even so, it seems plausible, when the rod is not completely locked, to frontally insert a bar into one of the clamps. Nevertheless, when a bar is inserted into one of the clamps, it is impossible to frontally introduce another bar or a pin into the second clamp.

The free ends of the jaws end in guide zones for the components to be introduced into the clamps. These guide zones, which are formed by a rounded or sloped area directed outwards, serve to guide a bar or a pin before it is clipped on, but do not limit the force to be produced to engage and introduce a bar into a clamp, which is required to move it apart.

SUMMARY OF THE INVENTION

Thus, the present invention proposes an orthopaedic attachment device that makes it possible to remedy the aforementioned drawbacks.

In this way, the orthopaedic attachment device according to the invention, may adopt at least two positions, namely an inoperative position and a locked position. The orthopaedic attachment device comprises two clamps mounted opposite each other through a resilient means, and held by a clamping rod, along a median axis, through through-holes, whereas each of the clamps consists of a body part that comprises an outer jaw and an inner jaw, connected by a joining wall, bounding an opening designed to receive a stiffening bar or a pin via an insert. The opening extends inwards from the clamp as far as the joining wall towards a passage and a hinge region, whereas in the inoperative position, the outer jaw is fixed, whereas the inner jaw is moveable inwards, namely towards the resilient means.

Let us add here that in the inoperative position, each of the inner jaws is directed outwards, namely towards the ends of the clamping rod.

We note here that in the inoperative position, the external surfaces of the moveable inner jaws make an acute angle that is directed outwards relative to the median axis of the clamping rod.

We point out here that the acute angle is between 80 and 88 degrees inclusive, preferentially between 82 and 87 degrees.

According to one characteristic, the outer end of each of the jaws comprises an engagement and positioning ramp of a stiffening bar or a pin via an insert, that appears as a surface that is perpendicular or substantially perpendicular to the median axis of the clamping rod.

According to one manner of embodiment, the difference in heights between the end and the center of an opening is between 5 and 25 percent, preferentially between 10 and 15 percent.

According to one additional characteristic, at the level of the passage, at least one jaw comprises a compression stop that extends at least as far as the jaw opposite to the one it is mounted on, more preferentially each of the jaws comprises a compression stop, with the compression stops being arranged opposite each other.

We note here that the external surfaces of the inner jaws each include a form-fitting cooperating means of assembly structure.

We point out here that the external surfaces each comprise a circular groove, circular grooves in which a resilient means is inserted, and which are arranged opposite each other.

BRIEF DESCRIPTION OF THE DRAWINGS

Other characteristics and advantages of the invention will emerge from the description that follows, by looking at the attached drawings which are given solely as non-limiting examples.

FIGS. 1 through 10 are views of the orthopaedic attachment device according to one manner of embodiment.
FIG. 1 is a perspective view.
FIG. 2 is a lateral view in the locked position.
FIG. 3 is a lateral view in the engaged position.
FIG. 4 is a lateral view in the inoperative position.
FIG. 5 is a rear view.
FIG. 6 is a section view of FIG. 5 according to F.
FIG. 7 is a lateral view of an attachment clamp.
FIG. 8 is a section view of a distal clamp, according to F.
FIG. 9 is a section view of a proximal clamp, according to F.
FIG. 10 is a top view of a clamp.

DETAILED DESCRIPTION OF THE INVENTION

Figure 1:
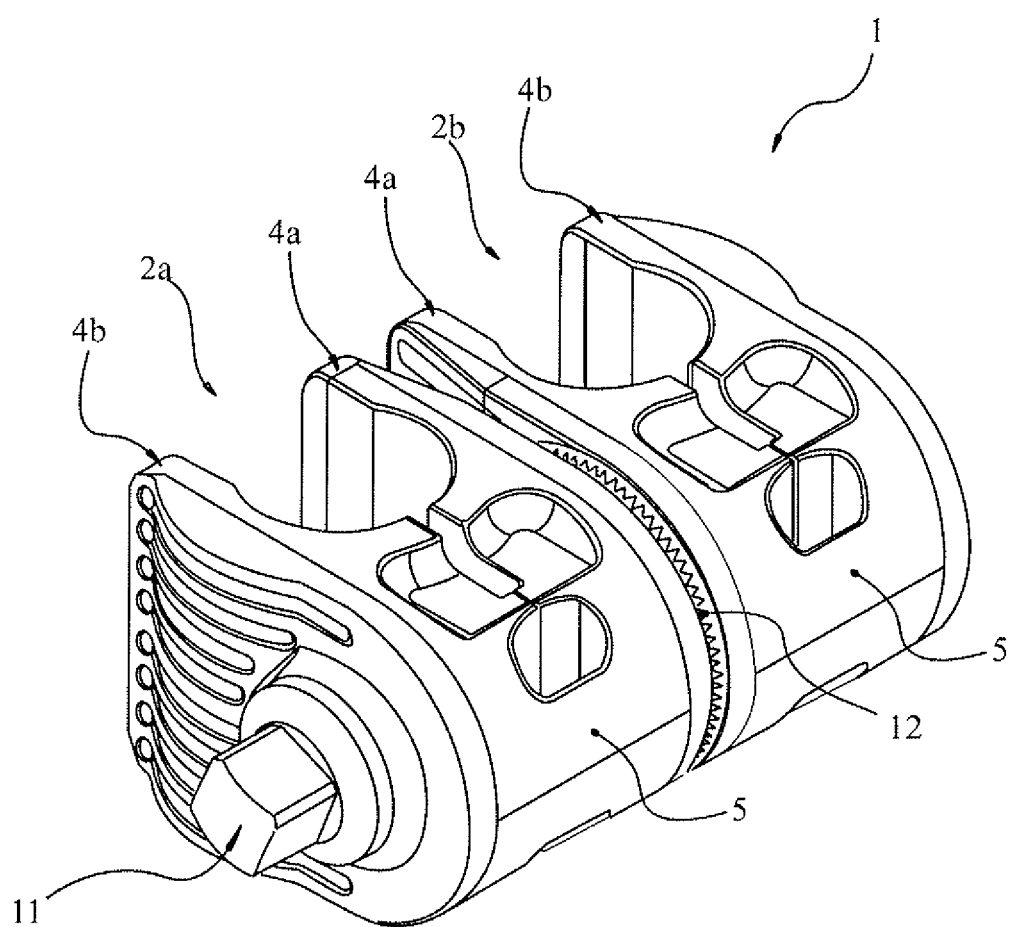
Figure 5:
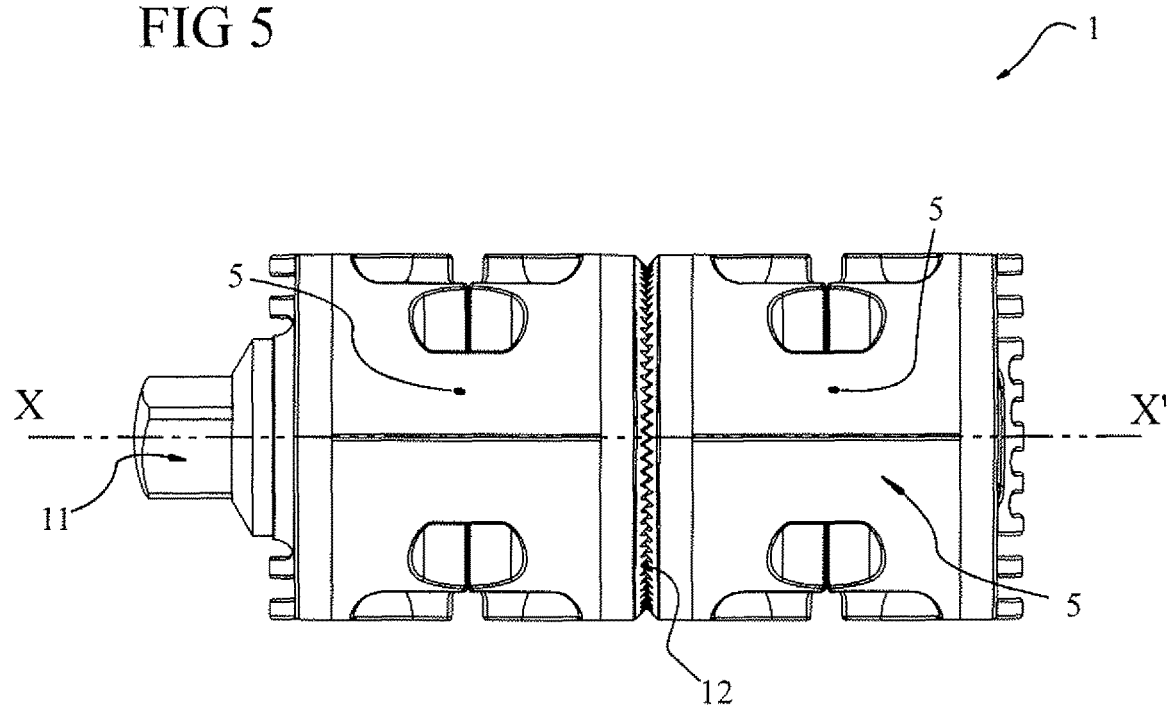
Figure 6:
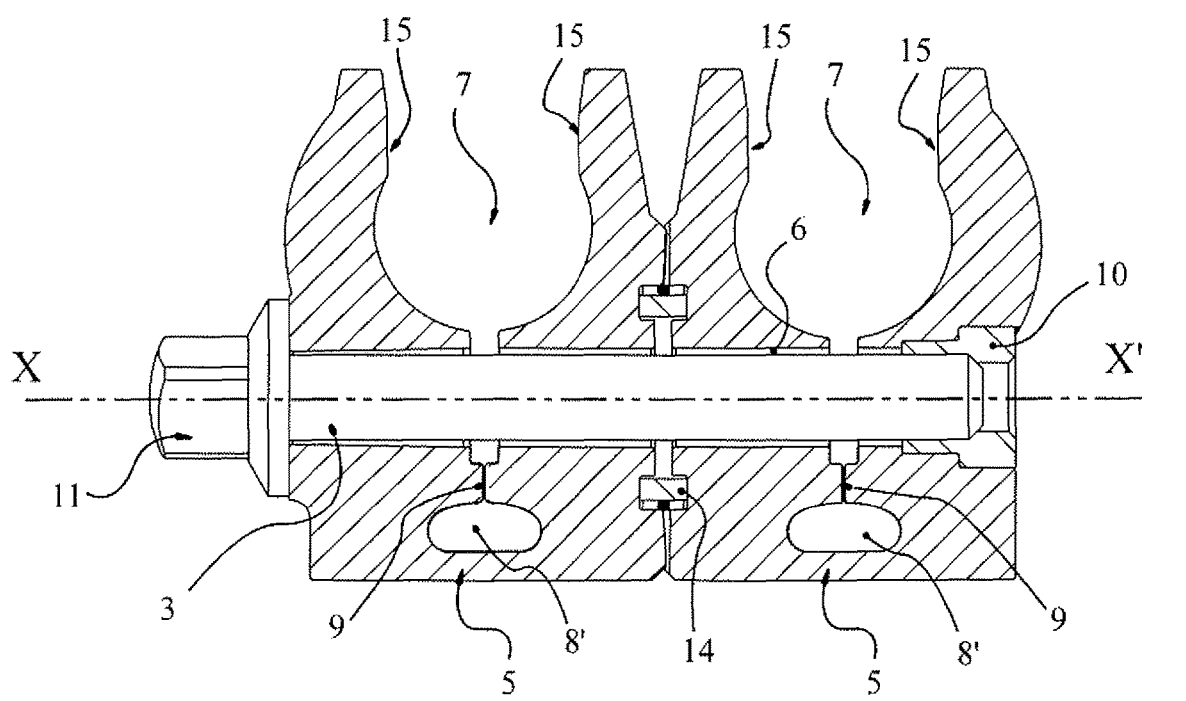

So, an orthopaedic attachment device (1), according to the invention, comprises, in a manner known in and of itself, of a pair of adjacent clamps (2), namely a clamp in a proximal position (2a) and a clamp in the distal position (2b), connected by a clamping rod (3) along a median axis (X, X'), threaded at one of its ends.

Let us add here that each of the clamps is made of a one-piece body, which comprises two jaws (4a, 4b), namely an inner jaw (4a) that is moveable inwards, towards the center of the clamping rod (3), and a fixed outer jaw (4b). The jaws (4a, 4b) of a clamp are arranged opposite each other, defining an opening (7) at one of their lateral ends and are connected by a joining wall (5) to their other lateral ends. These clamps (2a, 2b) each comprise a through-hole (6) in which the clamping rod (3) is inserted.

We note here that the opening (7) of a clamp (2) is extended by a passage (8) and a hinge region (8') that extends to the joining wall (5).

The proximal and distal positions are referenced relative to the head of the clamping rod (3).

The inner position corresponds to a position in the direction of the center of clamping rod (3), whereas an outer position corresponds to a position in the direction of the ends of clamping rod (3).

According to one characteristic, the fixed outer jaw (4b) of the distal clamp (2b) comprises, in its through-hole (6), a tapping that complements the threading of the clamping rod (3).

Figure 9:
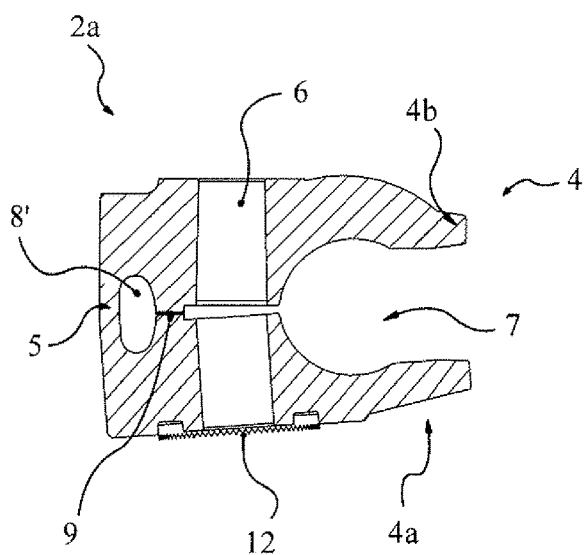

This tapping is preferably arranged in an insert (10) that is engaged, advantageously at the end, in a blind hole arranged in the through-hole (6) of outer jaw (4b) of the distal clamp (2b), as illustrated in FIG. 9.

Clamping rod (3) is implemented advantageously as a threading at one of its ends and a means of tightening, such as a bolted head (11), at its other end. The part of the clamping rod (3) that is located below the means of tightening, has a length that is advantageously less than or equal to the thickness of two fastening clamps (2), so that once the clamping rod (3) is fully inserted into the two clamps (2), it does not protrude from the attachment device (1).

It is understood that the clamping rod (3) may extend beyond clamps (2) and be held together by a bolt.

Figure 10:
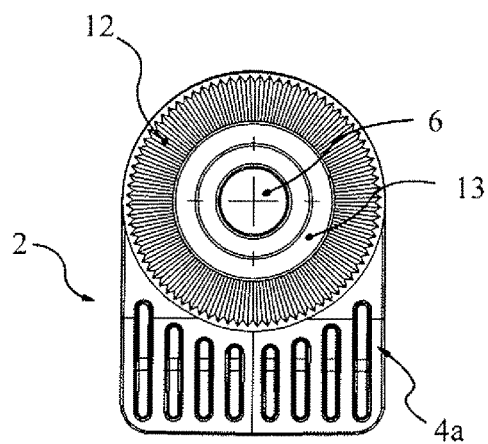

According to an additional characteristic, each of the external surfaces, of inner jaws (4a), comprises a form-fitting cooperating shape means of assembly, such as a striated disk, as illustrated in FIG. 10.

It should be noted that these external surfaces each comprise a circular groove (13) arranged opposite each other, in which a resilient means (14) is fitted.

According to the manner of embodiment illustrated, resilient means (14) appears as a hollow cylinder made of elastic material, which has a height greater than the total of the heights of the circular grooves (13) arranged opposite each of the clamps (2).

According to another manner of embodiment, the resilient means (14) is a spring.

When tightening occurs, the resilient means (14) becomes compressed in the circular grooves (13), until the form-fitting means of assembly (12) arranged on the external surfaces of clamps (2) come into contact and overlap one against the other, ensuring that a position is maintained under constraint of attachment clamps (2).

This tightening configuration makes it possible to reduce the bulk of the attachment device (1), through the assembly of two attachment clamps (2) against each other, without a separating part increasing the space between them.

The attachment device (1), according to the embodiment illustrated, in particular in FIG. 2, appears as only two clamps (2) mounted in cooperation with a clamping rod (3).

Let us restate here that each of the clamps (2) comprise a moveable inner jaw (4a) and a fixed outer jaw (4b) that define an opening (7) that is intended for the attachment of either a stiffening bar (16), or a pin (17) via an appropriate insert (18), as spelled out in greater detail later in the description.

Figure 7:
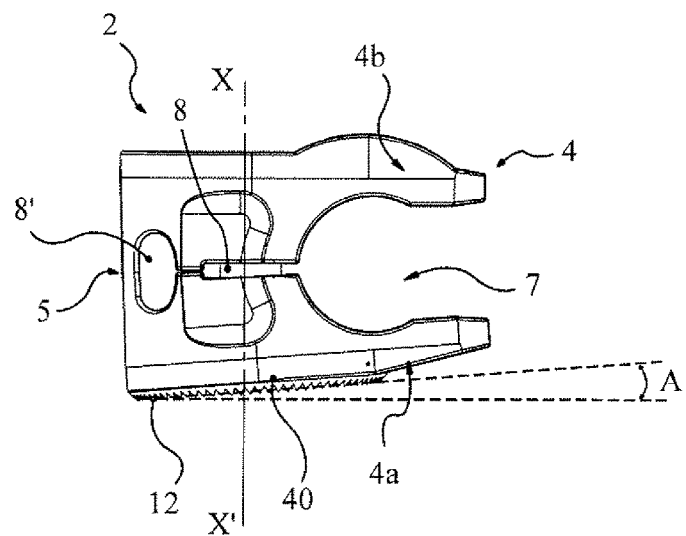
Figure 8:
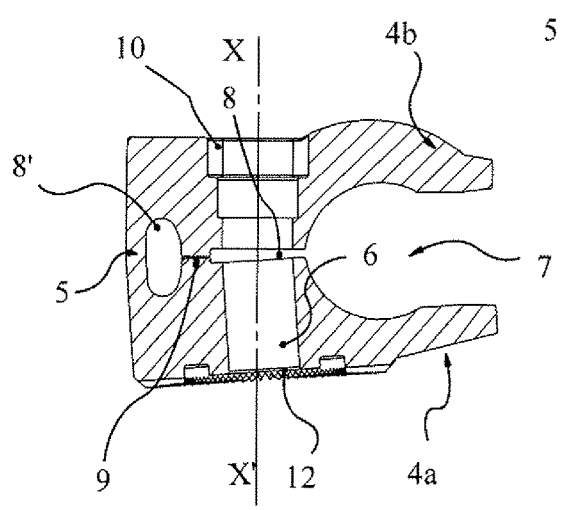

According to one characteristic, in the inoperative position, as spelled out in greater detail later in the description, the ends of the inner jaws are directed outwards, namely that the wall formed by the inner jaw (4a) is not perpendicular to the median axis (X, X'), but rather makes an acute angle (A) with this latter, as illustrated in FIG. 7. More precisely, the external surface (40) of the moveable inner jaw (4a) of each of the clamps (2), makes an acute angle (A) that is directed outwards relative to the median axis (X, X') of clamping rod (3).

According to the preceding characteristic, acute angle (A) is between 80 and 88 degrees inclusive, preferably between 82 and 87 degrees.

We note here that the outer jaw (4b) of the proximal clamp (2a) is considered to be fixed, given that it is locked in displacement by the bolted head (11) of clamping rod (3), whereas the outer jaw (4b) of the distal clamp (2b) is considered to be fixed, given that it is locked in displacement either by cooperation of the threading of the clamping rod (3) and of the tapping of the insert (10), or by cooperation of the threading of the clamping rod (3) and the tapping of a bolt.

The inner jaws (4a) of each of the clamps (2) are considered to be moveable, when the orthopaedic attachment device (1) is in the inoperative position, given the presence of the resilient means that enables clamps (2) to separate, leaving the inner jaws (4a) free to move inwardly, namely towards the center of the clamping rod (3), by the flexibility of their respective joining walls (5). The inner jaws (4a) are adapted for snapping on a stiffening bar (16) or a pin (17) via an insert (18).

We point out here that an opening (7) corresponds to the total of the semi-cylinder and a rectangular parallelepiped block corresponding to the dimensioning of the passage (8) between jaws (4).

More precisely, the diameter of opening (7), when a stiffening bar or a pin via an insert is held in a clamp (2), corresponds to the sum of the radii of two semi-cylinders plus the height of the passage (8).

We note here that in the inoperative position, the end of the inner jaw (4a) is directed outwards, passage (8) narrows in the direction of opening (7).

Let us add here that the orthopaedic attachment device (1) may adopt three positions, namely an inoperative position, an engaged position and a locked position.

The inoperative position corresponds to a position in which clamping rod (3) is engaged in the clamps (2), where clamping rod (3) is not completely locked, such that a gap is present between the two clamps (2), with the resilient means (14) not being fully compressed, and inner jaws (4a) of each of the clamps (2) are moveable. The clamps are held in their angular position relative to each other, and may be adjusted, by rotation of one of the clamps relative to each other.

The engaged position corresponds to a position in which each of the clamps holds a stiffening bar (16) or a pin (17) via an insert (18). The clamping rod (3) is in the same position as in the inoperative position. A gap is always present between the clamps (2), which is of course less than the gap in the inoperative position, since the moveable inner jaws (4a) are more open, namely the acute angles (A), from their external surfaces relative to the median axis (X, X'), being larger.

The locked position corresponds to the fully screwed-in clamping rod, with the resilient means (14) completely compressed, and with the form cooperation locking means (12) in contact and interlocked.

According to one additional characteristic, each of the jaws (4) is lengthened beyond the opening (7) by an engagement ramp (15) and a pre-positioning ramp, according to the manner of embodiment illustrated, where the engagement ramps (15) appear as parallel or substantially parallel walls, namely perpendicular or substantially perpendicular to the median axis (X, X').

As was previously introduced, in a common manner, the end of an opening of an attachment clamp ends abruptly by a rounding or a slope directed outwards. Passing a stiffening bar (16) or an insert (18) of a pin (17), from the outside to the inside of the opening of a clamp, is done in one step, quickly, creating strong vibrations in the pin(s) and therefore in the bones of the patient.

According to the invention, passing a stiffening bar (16) or an insert (18) of a pin (17) into these parallel engagement ramps (15) and pre-positioning ramps, causes jaws (4) to separate, towards a position of equilibrium, whereas the insertion of a stiffening bar or of a pin insert, into opening (7) is therefore done in two steps by progressive force, thus causing a more controlled insertion, limiting the engagement force and therefore limiting the resulting stresses for the patient.

In order to facilitate the insertion of a stiffening bar (16) or of a pin (17) insert (18) in an opening (7) and in this way further limit the stresses caused, the difference in height, between the center of opening (7), namely of the total of the semi-cylinders and the rectangular parallelepiped block corresponding to the dimension of passage (8), and the end of opening (7), namely between the engagement ramps (15), is between 5 and 25 percent, preferably between 10 and 20 percent, more preferentially between 10 and 15 percent.

As an example, according to the embodiment illustrated in FIG. 4, the difference in height between the end and the center of the opening (7), in the locked position, is around 12 percent.

The length of an engagement ramp (15) is between one-third and one times the radius of opening (7), namely between one-sixth and one-half of the height at the center of opening (7).

Let us add here that passage (8) is crossed by the clamping rod (3) and also features at least one compression stop (9) arranged on at least one of jaws (4).

It is understood that at least one compression stop (9) is located between the through-holes (6) and the joining wall (5), more precisely between the through-holes (6) and hinge (8'), at the level of passage (8).

At least one compression stop (9) is provided by a projection extending in a direction opposite of the jaw (4a, 4b) it is on. We point out here that the at least one compression stop (9) extends over the entire thickness of passage (8). In other words, in the inoperative position and in the locked position, at least one compression stop (9) connects the jaws (4) of a clamp (2) at the level of passage (8) that connects opening (7) at the joining wall (5).

We point out here that when in the engaged position, as illustrated in FIG. 3, at least one compression stop (9) is in the separated position at the level of passage (8).

According to one manner of embodiment, one of jaws (4a, 4b) comprises a compression stop (9) that extends to the other jaw (4a, 4b) arranged in correspondence, namely, extending at least over the entire thickness of passage (8).

According to the embodiment illustrated, two compression stops (9) are each located on one of the jaws (4) and come to rest against each other in opposition, with the total of the thicknesses of the compression stops (9) being greater than or equal to, preferentially largely equal to, the thickness of passage (8).

In this way, changing the engaged position to the locked position, occurs through the tightening of the rod (3), which causes, at the same time, the assembly and then an elastic deformation of at least one compression stop (9), preferentially assembly and deformation of two compression stops (9), and bending of the joining wall (5), which causes the inner jaws (4a) to align perpendicularly or largely perpendicularly with median axis (X, X') and thus the assembly and locking of the external surfaces of inner jaws (4a), one against the other, through locking the form-fitting means of assembly (12).

We note here that at least one compression stop (9) makes it possible to distribute the forces exerted when the rod (3) is tightened, and in this way limit the stresses exerted on the joining wall (5). We point out here that the absence of at least one compression stop (9) would result in the rupture of the joining wall (5) when the attachment clamps (2) are locked.

The invention claimed is:

1. An orthopaedic attachment device (1), configured to adopt at least two positions, namely an inoperative position and a locked position, which comprises two clamps (2a, 2b) mounted opposite each other through a resilient body (14) located between the two clamps, said two clamps held by a clamping rod (3) that extends along a median axis (X, X') into through-holes (6) defined in each of the two clamps, wherein each of the clamps (2a, 2b) comprises a body part that comprises an outer jaw (4b) and an inner jaw (4a), connected by a joining wall (5), said inner and outer jaws defining an opening (7) designed for receiving a stiffening bar (16) or a pin (17) and an insert (18), with said opening (7) extending towards the inside of the clamp (2a, 2b) as far as the joining wall (5) towards a passage (8) and a hinge region (8'), wherein in the inoperative position, each end of the inner jaws (4a) is directed towards the corresponding end of the clamping rod (3), the passage (8) shrinks as it extends away from the joining wall (5) in the direction of the opening (7), wherein the respective external surfaces (40) of the inner jaws that are oriented toward each other each comprise form-fitting cooperating shapes (12) that are: (i) disengaged from each other and diverge with respect to each other to allow rotation of said two clamps relative to each other about said clamping rod (3) when said device is in said inoperative position; and, (ii) interlocked with each other to prevent relative rotation between said two clamps about said clamping rod (3) when said device is in said locked position; and wherein said respective external surfaces (40) of the inner jaws (4a) that include said form-fitting cooperating shapes (12) each form an acute angle between themselves and the median axis (X, X') when said device is in said inoperative position.

2. The orthopaedic attachment device (1) according to claim 1, wherein the acute angle is between 80 and 88 degrees, inclusively.

3. The orthopaedic attachment device (1) according to claim 1, wherein the acute angle is between 82 and 87 degrees, inclusively.

4. The orthopaedic attachment device (1) according to claim 1, wherein an outer end of each of the jaws (4) comprises an engagement ramp (15) and a ramp for positioning a stiffening bar or a pin via an insert, which appears as a surface that is perpendicular or substantially perpendicular to median axis (X, X').

5. The orthopaedic attachment device (1) according to claim 1, wherein a difference in heights between an end and a center of each said opening (7) is in the range of 5 percent to 25 percent.

6. The orthopaedic attachment device (1) according to claim 1, wherein a difference in heights between an end and a center of each said opening (7) is in the range of 10 percent to 15 percent.

7. The orthopaedic attachment device (1) according to claim 1, wherein at least one jaw (4a, 4b) comprises a compression stop (9) that extends at least to the jaw (4a, 4b) opposite to the one it is mounted on.

8. The orthopaedic attachment device (1) according to claim 1, wherein each of the jaws (4a, 4b) comprises a compression stop (9), with the compression stops (9) being arranged opposite each other.

9. The orthopaedic attachment device (1) according to claim 1, wherein the external surfaces (40) each comprise a circular groove (13) arranged opposite each other and in which the resilient body (14) is located.

10. An orthopaedic attachment device adapted to be configured in an inoperative position or a locked position, said device comprising:
    two clamps (2a,2b) mounted adjacent each other with a resilient means (14) located between the two clamps, said clamps each comprising a through-hole (6) and held adjacent each other by a clamping rod (3) located in the through-holes and extending along a median axis (X,X');
    each of said two clamps comprising a body including an outer jaw (4b) and an inner jaw (4a) connected together by a joining wall (5), each of said two clamps defining an opening (7) adapted to receiving an associated bar or pin (16,17,18), said opening extending inwardly to the joining wall (5) through a passage (8) located between the inner and outer jaws such that a hinge region (8') is defined;
    the respective inner jaws (4a) of the two clamps (2a,2b) comprising respective external surfaces (40) oriented toward each other, said external surfaces (40) comprising cooperating shapes (12) that interlock when the external surfaces (4) are abutted and engaged with each other in said locked position;
    wherein said respective external surfaces (40) of said two clamps on which the cooperating shapes (12) are located are angled relative to each other and each form an acute angle relative to said median axis (X,X') when the orthopaedic device is in the inoperative position such that the external surfaces including said cooperating shapes diverge relative to each other as they extend outwardly away from said clamping rod and such that each external surface (40) that includes said cooperating shapes defines an acute angle between itself and the median axis (X,X');
    wherein the form-fitting cooperating shapes (12) of the respective external surfaces (40): (i) are disengaged from each other and diverge with respect to each other to allow rotation of said two clamps relative to each other about said clamping rod (3) when said device is in said inoperative position; and, (ii) are abutted and interlocked with each other to prevent relative rotation between of said two clamps about said clamping rod (3) when said device is in said locked position.

11. The orthopaedic attachment device as set forth in claim 10, wherein the acute angle is in the range of 80 degrees to 88 degrees.

12. The orthopaedic attachment device as set forth in claim 10, wherein the acute angle is in the range of 82 degrees to 87 degrees.

13. The orthopaedic attachment device as set forth in claim 10, wherein an outer end of each of the outer jaws and each of the inner jaws comprises an engagement ramp (15) comprising a surface that is oriented at least substantially perpendicular with respect to the median axis.

14. The orthopaedic attachment device as set forth in claim 10, wherein an outer end of each of the outer jaws and each of the inner jaws comprises an engagement ramp (15) and wherein a difference in height between an end of the opening that is defined between the engagement ramps and a center of the opening is in the range of 5 percent to 25 percent.

15. The orthopaedic attachment device as set forth in claim 10, wherein an outer end of each of the outer jaws and each of the inner jaws comprises an engagement ramp (15) and wherein a difference in height between an end of the opening that is defined between the engagement ramps and a center of the opening is in the range of 10 percent to 15 percent.

16. The orthopaedic attachment device as set forth in claim 10, wherein at least one of the inner and outer jaws of each of the two clamps comprises a compression stop (9) that extends toward the other one of the inner and outer jaws.

17. The orthopaedic attachment device as set forth in claim 10, wherein each of the inner and outer jaws of each of the two clamps comprises a compression stop (9), wherein the compression stops of the inner and outer jaws are arranged opposite each other.

18. The orthopaedic attachment device as set forth in claim 10, wherein the clamping rod (3) includes a driving head (11) at a first end and comprises threads at a second end opposite the first end, and wherein the second end of the clamping rod is threadably engaged with the outer jaw of a distal one (2b) of the two clamps (2a,2b).

19. The orthopaedic attachment device as set forth in claim 10, wherein the passage (8) of each of said two clamps narrows as it extends away from said joining wall (5) toward said opening (7) when said orthopaedic device is in its inoperative position.

* * * * *